United States Patent
Solem et al.

(10) Patent No.: US 10,391,225 B2
(45) Date of Patent: Aug. 27, 2019

(54) APPARATUS FOR EXTRACORPOREAL BLOOD TREATMENT AND A CONTROL METHOD THEREFOR

(71) Applicant: GAMBRO LUNDIA AB, Lund (SE)

(72) Inventors: Kristian Solem, Kavlinge (SE); David Stefani, Modena (IT); Sture Hobro, Lund (SE); Bo Olde, Lund (SE)

(73) Assignee: Gambro Lundia AB, Lund (SE)

( * ) Notice: Subject to any disclaimer, the term of this patent is extended or adjusted under 35 U.S.C. 154(b) by 499 days.

(21) Appl. No.: 15/104,861

(22) PCT Filed: Dec. 9, 2014

(86) PCT No.: PCT/EP2014/076956
§ 371 (c)(1),
(2) Date: Jun. 15, 2016

(87) PCT Pub. No.: WO2015/091082
PCT Pub. Date: Jun. 25, 2015

(65) Prior Publication Data
US 2016/0310657 A1  Oct. 27, 2016

(30) Foreign Application Priority Data
Dec. 18, 2013 (EP) ..................................... 13197966

(51) Int. Cl.
*A61M 1/36* (2006.01)
*G01F 23/14* (2006.01)
*G01F 23/18* (2006.01)

(52) U.S. Cl.
CPC .......... *A61M 1/3627* (2013.01); *A61M 1/367* (2013.01); *A61M 1/3624* (2013.01);
(Continued)

(58) Field of Classification Search
CPC .............. A61M 1/3627; A61M 1/3624; A61M 1/3626; A61M 1/367; G01F 23/14; G01F 23/18
See application file for complete search history.

(56) References Cited

U.S. PATENT DOCUMENTS

| | | |
|---|---|---|
| 7,013,727 B2 | 3/2006 | Delnevo |
| 8,430,834 B2 | 4/2013 | Kopperschmidt |

(Continued)

FOREIGN PATENT DOCUMENTS

| | | | |
|---|---|---|---|
| CN | 101516418 A | | 8/2009 |
| EP | 2823834 | * | 1/2015 |
| WO | 2010/142394 A1 | | 12/2010 |

OTHER PUBLICATIONS

International Search Report PCT/EP2014/076956—dated Feb. 27, 2015—5 pages.

(Continued)

*Primary Examiner* — Ariana Zimbouski
(74) *Attorney, Agent, or Firm* — K&L Gates LLP

(57) ABSTRACT

An apparatus (1) is described for extracorporeal blood treatment, comprising a treatment unit (2), an extracorporeal blood circuit (8) and a fluid evacuation line (10). A venous chamber (12) is placed in a blood return line (7) and is arranged in use to contain a gas in an upper portion (120) and blood at a predetermined level in a lower portion. The apparatus (1) comprises a control unit (21) connected to a first pressure sensor (14) and configured to: receive from the first pressure sensor (14) a first signal ($P1(t)$) relating to a time variable pressure ($P(t)$) of the blood flow; calculate a phase shift ($\theta$) between the first signal ($P1(t)$) and a reference signal ($P2(t)$) correlated to the time variable pressure ($P(t)$) detected at a location distinct from the upper portion (120) of the chamber (12); monitor the volume (V) of gas in (Continued)

the upper portion (120) of the chamber (12) through the phase shift (θ).

26 Claims, 5 Drawing Sheets

(52) U.S. Cl.
CPC .......... *A61M 1/3626* (2013.01); *G01F 23/14* (2013.01); *G01F 23/18* (2013.01); *A61M 2205/123* (2013.01); *A61M 2205/3331* (2013.01); *A61M 2205/3386* (2013.01); *A61M 2205/3389* (2013.01)

(56) References Cited

U.S. PATENT DOCUMENTS

| | | | |
|---|---|---|---|
| 8,617,093 | B2 | 12/2013 | Kopperschmidt et al. |
| 9,750,865 | B2* | 9/2017 | Vasta ..................... A61M 1/16 |
| 9,770,546 | B2* | 9/2017 | Vasta ..................... A61M 1/16 |
| 2005/0119600 | A1 | 6/2005 | Lucke et al. |
| 2011/0257578 | A1 | 10/2011 | Zanotti et al. |
| 2011/0257579 | A1 | 10/2011 | Rossi et al. |

OTHER PUBLICATIONS

Written Opinion of the International Searching Authority PCT/EP2014/076956—dated Feb. 27, 2015—6 pages.

Prosecution history of U.S. Appl. No. 13/001,314 (now issued U.S. Pat. No. 9,442,036) filed Dec. 23, 2010.
Prosecution history of U.S. Appl. No. 13/380,631 (now issued U.S. Pat. No. 9,433,356) filed Mar. 16, 2012.
Prosecution history of U.S. Appl. No. 14/129,087 (now issued U.S. Pat. No. 9,427,513) filed Apr. 11, 2014.
Prosecution history of U.S. Appl. No. 12/988,146 (now issued U.S. Pat. No. 8,718,957) filed Oct. 15, 2010.
Prosecution history of U.S. Appl. No. 13/000,856 (now issued U.S. Pat. No. 8,715,216) filed Dec. 22, 2010.
Prosecution history of U.S. Appl. No. 14/270,246 (now issued U.S. Pat. No. 9,383,288) filed May 5, 2014.
Prosecution history of U.S. Appl. No. 13/519,532, filed Sep. 12, 2012.
Prosecution history of U.S. Appl. No. 14/123,397, filed Dec. 2, 2013.
Prosecution history of U.S. Appl. No. 13/519,483, filed Sep. 13, 2012.
Prosecution history of U.S. Appl. No. 13/519,559, filed Sep. 12, 2012.
Prosecution history of U.S. Appl. No. 14/234,527, filed May 5, 2014.
Prosecution history of U.S. Appl. No. 14/408,849, filed Dec. 17, 2014.
Prosecution history of U.S. Appl. No. 14/651,730, filed Jun. 12, 2015.
Prosecution history of U.S. Appl. No. 14/777,695, filed Sep. 17, 2015.
Prosecution history of U.S. Appl. No. 14/917,099, filed Mar. 7, 2016.

* cited by examiner

APPARATUS FOR EXTRACORPOREAL BLOOD TREATMENT AND A CONTROL METHOD THEREFOR

PRIORITY CLAIM

The present application is a National Phase of International Application No. PCT/EP2014/076956, filed on Dec. 9, 2014, which claims priority to European Patent Application No. 13197966.8, filed Dec. 18, 2013, the entire contents of each of which are incorporated herein by reference and relied upon.

FIELD OF THE INVENTION

The present invention relates to an apparatus for extracorporeal blood treatment and also to a control method of the apparatus.

BACKGROUND OF THE INVENTION

Known apparatuses for extracorporeal treatment of blood include at least one treatment unit (for example a dialyzer or a filter, or an ultra-filter or a plasma filter or a filter unit of any other nature) having a semipermeable membrane which separates the treatment unit into two chambers. An extracorporeal blood circuit allows the circulation of blood taken from a patient through the first chamber of the treatment unit. At the same time, and typically in a counter-current direction to the blood flow, a treatment fluid is circulated through a special circuit in the second chamber of the treatment unit. This type of equipment for blood treatment may be used for the removal of solutes and excess fluid from the blood of patients suffering from renal failure.

The extracorporeal blood circuit also includes an arterial and a venous chamber, also called bubble-traps, respectively located on a blood removal line from the patient and on a return blood line to the patient. The venous and arterial chambers, during the treatment, contain a predetermined quantity of blood so that the chambers are filled to certain levels (depths), and a predetermined quantity of gas (air) in the remaining part of the chamber. For a safe operation of the extracorporeal treatment, the level of blood should never fall below a critical minimum level that could lead to the introduction of air into the extracorporeal circulation lines and subsequent potential infusion of the air into the circulatory system of the patient, with serious consequences.

Since the risks of such an event exist, and the problems caused to the patient are extremely serious, if not critical, the known extracorporeal blood treatment machines are equipped with safety systems that may detect such an event and, should it occur, place the patient in safety. In particular, on the return blood line that returns blood back to the patient, upstream the vascular access and downstream of the venous chamber, a device is present which is directly connected to the control unit of the machine and configured for the detection of air bubbles in the blood. In the event of a bubble of air is detected in the venous line, the control unit activates a patient safety procedure for the "isolation" of the patient by at least closing clamps on the extracorporeal blood circuit and/or shutting down the blood pump.

In addition to this safety device, some machines are also equipped with appropriate blood level sensors in the venous chamber (more rarely also in the arterial chamber). Such blood level sensors signal when a minimum level is reached that requires intervention of specialized personnel to restore the correct quantity of blood in the chamber such as to avoid risks to the patient.

These systems, while fulfilling the tasks for which they are designed, incur additional costs and require changes to the hardware of a machine on which they are or are to be installed. Particularly because of the cost, these security systems are generally present only on the return line of the blood, downstream of the treatment unit.

Furthermore, it is also worth mentioning that bubble sensors are generally able to reliably detect only bubbles of a certain size, while they are substantially insensitive to micro-bubbles dissolved in blood. Although in the past dissolved micro-bubbles were not considered dangerous to patients, recent studies (e.g. "Microemboli, developed during hemodialysis, pass the lung barrier and may cause ischemic lesions in organs such as the brain" from journal "NDT Nephrology Dialysis Transplantation", Volume 25, issue 8, pages 2691-2695, August 2010, by Ulf Forsberg, Per Jonsson, Christofer Stegmayr and Bernd Stegmayr) have linked some typical disorders of chronic patients—such as pulmonary hypertension and other ischemic problems—to the quantity of air, in the form of micro-bubbles, generated during dialysis and not detected by current safety systems.

It should be noted in this regard that generation of micro-bubbles mainly occurs because of the entry of air into the blood removal line, for example due to a low level of blood in the arterial blood chamber. A low level of blood may for instance be caused by insufficient machine priming or by an infusion. Bubbles may then get into the bloodstream and reach the dialyzer, which micronizes the air bubbles making them difficult to detect with conventional sensors.

In order to address the problem of determining and monitoring blood levels in blood chambers, U.S. Pat. No. 7,013,727 discloses a method for determining the blood level in a chamber used in dialysis machines which applies the ideal gas law. According to this patent, a change in the volume occupied by the gas in the chamber is linked to pressure and the level of blood in the chamber is detected. This methodology, while enabling blood level determination without using a level sensor, requires additional hardware (a further sensor) in addition to that already present on the machine.

SUMMARY

There is, therefore, a need for an apparatus for blood treatment that is able to detect a variation in the volume of gas and in the blood level in venous and arterial chambers which may be an indication of potential entry of air into the extracorporeal blood circuit. Further, there is a need for an apparatus which may perform blood level monitoring without the need for additional dedicated hardware. There is also a need for enabling level monitoring in the venous chamber and possibly also in the arterial chamber to support the safety systems already present in the machine. Furthermore, there is a need for using aspects of the invention on conventional blood treatment machines simply by updating the operating software thereof. In addition, there is a need for an apparatus that reliably performs, lowering the number of false positives and increasing detection of risk situations.

At least one of the above-indicated needs is substantially met by a blood treatment apparatus according to one of more of any of the accompanying claims. Aspects of the invention are illustrated in the following.

In a first independent aspect of the invention, an apparatus is provided for extracorporeal blood treatment comprising:

at least one treatment unit comprising at least a first compartment;
at least one blood removal line connected to the first compartment and configured to remove blood from a patient;
at least one blood return line connected to the first compartment and configured to return treated blood to the patient; the blood removal line, the blood return line and the first compartment being part of an extracorporeal blood circuit;
at least one chamber placed in the extracorporeal blood circuit, the chamber being arranged in use to contain a volume V of gas in an upper portion and blood at a predetermined level in a lower portion;
at least one blood pump operating at the extracorporeal blood circuit and configured to move blood in the circuit;
at least a first pressure sensor associated to the upper portion of the chamber and configured to enable determining pressure values internally of the upper portion;
a control unit connected to the first pressure sensor and to the pump, and configured to:
 receive from the first pressure sensor a first signal $P1(t)$ relating to at least one pulse of pressure of the blood flow;
 calculate a phase shift $\theta$ between the first signal $P1(t)$ and a reference signal $P2(t)$ correlated to said pulse of pressure detected at a location distinct from the upper portion of the chamber, said phase shift $\theta$ depending on the volume V of gas in the upper portion of the chamber; and
 monitor said volume V of gas through said phase shift $\theta$.

The pulse of pressure may be part of a time-variable (pulsating/oscillating) pressure $P(t)$ of the blood flow.

In a second aspect of the invention, a method is provided for detecting level variations of the blood level in chambers used in apparatus for extracorporeal blood treatment and/or a method for reducing the risk of infusion bubbles of gas into a patient in apparatus for extracorporeal blood treatment, comprising:
at least one treatment unit comprising at least a first compartment;
at least one blood removal line connected to the first compartment and predisposed to remove blood from a patient;
at least one blood return line connected to the first compartment and predisposed to return treated blood to the patient; the blood removal line, the blood return line and the first compartment being part of an extracorporeal blood circuit;
at least one chamber placed in the extracorporeal blood circuit, the chamber being arranged in use to contain a volume V of gas in an upper portion and blood at a predetermined level in a lower portion;
at least one blood pump operating at the extracorporeal blood circuit such as to move the blood in the circuit;
at least a first pressure sensor associated to the upper portion of the chamber and configured such as to enable determining pressure values internally of the upper portion;
a control unit connected to the first pressure sensor and to the pump; the method comprising carrying out a control procedure comprising:
 receiving from the first pressure sensor a first signal $P1(t)$ relating to at least one pulse of pressure of the blood flow;
 calculating a phase shift $\theta$ between the first signal $P1(t)$ and a reference signal $P2(t)$ correlated to said pulse of pressure detected at a location distinct from the upper portion of the chamber associated to the first pressure sensor, said phase shift $\theta$ depending on volume V of gas in the upper portion of the chamber;
 monitoring said volume V through said phase shift $\theta$.

The treatment unit may comprise at least a first compartment and at least a second compartment separated from one another by a semipermeable membrane; wherein the blood removal line is connected to an inlet port of the first compartment and predisposed to remove blood from a patient and the blood return line is connected to an outlet port of the first compartment and predisposed to return treated blood to the patient.

The treatment unit may also be an adsorption column for performing adsorption therapies.

At least one fluid evacuation line may be connected to an outlet port of the second compartment, wherein the fluid evacuation line and the second compartment are part of a treatment fluid circuit.

The "fluid compliance" or "hydraulic capacitance" of a system made of liquid and gas in pipes and chambers is given by the decrease in system volume per change in pressure. The compliance is related to both the physical rigidity of the liquid as well as the physical rigidity of its encapsulating material and/or gas bubbles in the liquid and/or other elements acting on the liquid such as a cushion of gas above the liquid. Also, if a liquid system has bubbles, the bubbles play the role of a flexible encapsulating material, and from the standpoint of liquid flow, a small tube with bubbles inside has large compliance. So also a rigid container with an upper air volume above the liquid has a large compliance.

In the present apparatus and method the fluid compliance of the blood circuit is mainly due to the cushion of air/gas contained in the upper portion, above the blood level.

This compliance is proportional to the volume of said cushion of air/gas.

Usually, the total volume of said chambers is comprised between about $0 \text{ cm}^3$ and $200 \text{ cm}^3$ and the volume of air/gas is comprised between about 5% and 75% of the total volume of the chamber.

Any change in the fluid compliance provided by other parts of the circuit, such as by the treatment unit, by the bubbles inside the flow of blood, by the flexibility of the pipes, by the stiffness of the chamber walls, is negligible with respect to the change in the fluid compliance due to variations of the volume of air/gas in said chambers.

The fluid compliance of the chamber is function of and depends mainly on the volume of gas in the upper portion of the chamber.

The phase shift is function of said fluid compliance.

In this regard, considering a simplified blood circuit comprising one peristaltic pump and a tract of tubing provided with a single chamber only (containing a gas in an upper portion and blood at a predetermined level in a lower portion) and considering the electrical analogy of said circuit (in which the effect of inertia of the fluid has been neglected):
 electrical current, (I)—fluid volume flow, (Q);
 electrical voltage (U)—fluid pressure (P);
 electrical resistance, (R)—fluid resistance, (R);
 electrical capacitance, (C)—fluid compliance, (C);
the relation between the fluid pressure/voltage U in the chamber and the fluid pressure/voltage Uo at the pump (in the frequency domain) is:

$$U = 1/(j*\omega*C)/(1/(j*\omega*C)+R)*Uo$$

where $1/(j*\omega*C)$ is the Fourier transformation of C (R remains unchanged) and $\omega$ is the angular frequency in [rad/s] of the pressure pulses.

The phase shift $\theta$ of U compared to Uo is:

$$\theta = \arctan(-\omega*R*C)$$

It follows that the phase shift is function of the volume of gas V in the upper portion of the chamber:

$$\theta = \arctan(-\omega*R*k*V/P)$$

where $C=k*V/P$, P is an average pressure in the chamber and k depends on the geometry of the chamber.

In a 3rd aspect according to at least one of the previous aspects, monitoring the volume V of gas in the upper portion of the at least one chamber comprises: calculating the volume V of gas in the upper portion of the chamber from said phase shift $\theta$.

Measuring the phase shift $\theta$ allows to calculate the volume V: $V=f1(\theta)$, where f1 is known and provided that $\omega$, k and R are known too.

In a 4th aspect according to the previous aspect, f1 is obtained through empirical tests, like a function comprising experimentally-determined constants or an experimentally-determined correlation table.

Indeed, this simplified model cannot be applied to all the real apparatuses.

Therefore, it is easier to define the relation between the phase shifts and the volumes through the 4th aspect above.

In a 5th aspect according to at least one of the previous aspects, monitoring the volume V of gas in the upper portion of the chamber comprises:
setting a desired phase shift $\theta'$ corresponding to a desired volume $V'$ of gas in the upper portion of the chamber;
comparing the calculated phase shift $\theta$, corresponding to the volume V of gas in the upper portion of the chamber, with the desired phase shift $\theta'$.

In a 6th aspect according to at least one of the previous aspects, the reference signal is a timing of the control signal of the blood pump.

In a 7th aspect according to at least one of the previous aspects from 1st to 5th, the reference signal is a timing of the speed signal of the blood pump.

The blood pump, being a peristaltic pump, generates pressure pulses in the blood and a timing of the control and/or speed signals of the pump is (or is correlated to) the timing of the pulses of pressure in the blood flow.

In this way, data from only one pressure sensor is needed to monitor the volume V of gas in the upper portion of the chamber through the phase shift $\theta$.

In a 8th aspect according to at least one of the previous aspects from 1st to 5th, the reference signal $P2(t)$ is a pressure signal of a second pressure sensor associated with the extracorporeal blood circuit.

In a 9th aspect according to the previous aspect, the second pressure sensor 13 is associated directly to the blood flow and measures the pulse of pressure with no delay or with negligible delay with respect to the generation of said pulse in the blood and the first pressure sensor measures the same pulse of pressure in the upper portion of the chamber. The relation f1 between volumes V and phase shifts $\theta$ for that apparatus is known and therefore the volume V can be calculated through $V=f1(\theta)$.

The reference signal may also be a pressure signal of a second pressure sensor associated with the treatment fluid circuit such as with the evacuation line.

In a 10th aspect according to any one of the preceding aspects, the at least one chamber is a venous chamber placed downstream of the treatment unit. Monitoring the volume V1 (and/or the level L1) of blood in the venous chamber allows to predict imminent emptying of the same and avoids subsequent potential infusion of air into the circulatory system of the patient. This allows to calculate the gas volume at a different pressure in order to alert/counter-act on a predicted risk situation. This also allows to calculate the volume of the gas at the pressure when the blood pump is running at lower rate or is stopped (assuming that the amount of gas is unchanged). This can be used for giving an indication of the risk for infusing gas to the patient. A theoretical example: Vp (average)=+300 mmHg at Qb=500 ml/min and 90% of venous chamber is filled with gas. If the blood pump is stopped and the average pressure becomes 0 mmHg, the gas volume would become 125% of the venous chamber and apparently extend beyond the air detector. In order to assure that no air is leaving the venous chamber under these conditions, the gas volume at 300 mmHg should not exceed about 70% of the venous chamber's volume.

Furthermore, monitoring the volume V1 (and/or the level L1) of blood in the venous chamber allows to avoid the level going to high and wetting the hydrophobic filter of said chamber which protects the air/gas pressure sensor. Furthermore, monitoring the volume V1 (and/or the level L1) of blood in the venous chamber allows to have a minimum air in said chamber (enough to allowing degassing and not wetting the filter). Minimum air in the venous chamber minimize the number of small bubbles reaching the patient and maximizes the pulsating heart signal of the patient in the venous chamber (this is essential for patients with a weak heart pulsation). The minimum volume of air in said venous chamber may be kept between about 5% and about 15% of the total volume of said chamber. The heart signal can be also used to supervise and detect a venous needle dislodgement. Indeed, one of the most important damping factors for the heart signal is the air in the venous chamber and if this is minimized the possibility of detecting a patient is increased.

In a 11th aspect according to any one of the preceding aspects, the chamber is an arterial chamber placed upstream of the blood pump.

In a 12th aspect according to any one of the preceding aspects, the chamber is an expansion chamber placed between the blood pump and the inlet port of the first compartment.

In a 13th aspect according to the 8th aspects, the extracorporeal blood circuit comprise a first chamber and a second chamber, wherein the first pressure sensor is associated to the upper portion of the first chamber and the second pressure sensor is associated to the upper portion of the second chamber.

In a 14th aspect according to the previous aspect, the control unit is configured to monitor the volume V1 of gas in the upper portion of the first chamber and the volume V2 of gas in the upper portion of the second chamber through said phase shift $\theta$.

In this regard, considering a simplified blood circuit comprising one peristaltic pump and a tract of tubing provided with the first chamber downstream of the pump and the second chamber upstream of the pump and considering the electrical analogy of said circuit (in which the effect of the inertia of the fluid has been neglected):

Uo/Po electrical voltage/fluid pressure at the pump;
U1/P1 electrical voltage/fluid pressure in the first chamber;

U2/P2 electrical voltage/fluid pressure in the second chamber;

R1 electrical resistance/fluid resistance of the first chamber;

R2 electrical resistance/fluid resistance of the second chamber;

C1 electrical capacitance/fluid compliance of the first chamber which is function of the volume V1;

C2 electrical capacitance/fluid compliance of the second chamber is function of the volume V2;

the relations between the fluid pressures/voltages U1, U2 in the two chambers and the fluid pressure/voltage Uo at the pump (in the frequency domain) are:

$$U1=1/(j*\omega*C1)/(1/(j*\omega*C1)+R1)*Uo$$

$$U2=1/(j*\omega*C2)/(1/(j*\omega*C2)+R2)*Uo$$

and the phase shifts of U1 and U2 compared to U0 are $$\theta1=\arctan(-\omega*R1*C1)$$

$$\theta2=\arctan(-\omega*R2*C2)$$

It follows that the phase shift between the pulse of pressure when sensed by the second pressure sensor (reference signal P2(t)) in the second chamber and the pulse of pressure when sensed by the first pressure sensor (first signal P1(t)) in the first chamber is:

$$\theta=\theta1-\theta2=(\arctan(-\omega*R1*C1)-\arctan(-\omega*R2*C2))$$

wherein $$C1=k1*V1/P1$$

$$C2=k2*V2/P2$$

Since C1 is function of V1 and C2 is function of V2, the phase shift θ depends on V1 and V2.

Assuming the geometry of the chambers is such that R1 and R2 are equal and set to R:

$$\theta=(\arctan(-\omega*R*k1*V1/P1)-\arctan(-\omega*R*k2*V2/P2)) \quad 1)$$

If the volume of gas (and the average pressures P1, P2) in each chamber is the same (V1=V2) and k1=k2 then the phase shift θ is equal to zero (θ=0). Any misalignment between the levels/pressures of the chambers gives rise to a change of phase shift θ.

In a 15th aspect according to the previous aspect, the control unit is configured to calculate magnitudes |P1|, |P2| of the signals P1(t), P2(t) in the chambers.

In a 16th aspect according to the previous aspect, the control unit is configured to calculate the volume V1 of gas in the upper portion of the first chamber and the volume V2 of gas in the upper portion of the second chamber through said magnitudes |P1|, |P2|.

The magnitude of signals |P1| and |P2| generated by each sensor when sensing the pulse of pressure depend too on the fluid compliances and relates to U0 (pressure P0) as:

$$|P1|=\mathrm{sqrt}(1/(1+(\omega*R*C1)^2))*|U0|$$

$$|P2|=\mathrm{sqrt}(1/(1+(\omega*R*C2)^2))*|U0|$$

It follows that:

$$|P1|/|P2|=\mathrm{sqrt}((1+(\omega*R*k2*V2/P2)^2)/(1+(\omega*R*k1*V1/P1)^2)) \quad 2)$$

In a 17th aspect according to the previous aspect, the control unit is configured to calculate the volume V1 of gas in the upper portion of the first chamber and the volume V2 of gas in the upper portion of the second chamber from the phase shift θ, the average pressures P1, P2 and the magnitudes of said pressures |P1|, |P2|.

By solving the equations 1) and 2) above, V1 and V2 can be calculated provided that ω, k1, k2 and R are known.

In a 18th aspect according to the previous aspects from 1st to 12th, the extracorporeal blood circuit comprise a first chamber and a second chamber wherein the first pressure sensor is associated to the upper portion of the first chamber and the gas/air amount in the second chamber remains substantially unchanged during treatment so that the volume V is calculated through V=f1(θ), where f1 is known.

In a 19th aspect according to the 13th or the 14th aspect, the control unit is configured to:

set the angular frequency ω of the pump at a first level ωa;

measure a first value θa of said phase shift θ at the first frequency level ωa; set the angular frequency ω of the pump at a second level ωa;

measure a second value θa of said phase shift θ at the second frequency level ωb;

measure the average pressures P1a, P2a, P1b, P2b in the first and second chambers at each of the two frequency levels ωa, ωb;

calculate the volumes V1a, V1b, V2a, V2b of gas in the first and second chambers at the two frequency levels ωa, ωb from the measured values θa, θb of the phase shift.

In a 20th aspect according to the previous aspect, the volumes are calculated by applying the ideal gas law.

In a 21th aspect according to the previous aspect, the volumes are calculated through:

$$\theta a=(\arctan(-\omega a*R*C1a)-\arctan(-\omega a*R*C2a))$$

$$\theta b=(\arctan(-\omega b*R*C1b)-\arctan(-\omega b*R*C2b))$$

$$P1a*V1a=P1b*V1b$$

$$P2a*V2a=P2b*V2b$$

the fluid compliances being:

$$C1a=k1*V1a/P1a$$

$$C1b=k1*V1b/P1b$$

$$C2a=k2*V2a/P2a$$

$$C2b=k2*V2b/P2b$$

In a 22th aspect according to the 13th or the 14th aspect, the control unit is configured to:

measure the phase shifts θ1 of a first harmonic ω1 of the signals P1(t), P2(t);

measure the phase shifts θ2 of a second harmonic ω2 of the signals P1(t), P2(t);

calculate the volumes V1, V2 of chambers from the measured phase shifts θ1, θ2 through:

$$\theta1=(\arctan(-\omega1*R*C1)-\arctan(-\omega1*R*C2))$$

$$\theta2=(\arctan(-\omega2*R*C1)-\arctan(-\omega2*R*C2))$$

the fluid compliances being:

$$C1=k1*V1/P1$$

$$C2=k2*V2/P2$$

In a 23rd aspect according to anyone of the previous aspect from 13th to 22th, the first chamber is a venous chamber placed downstream of the treatment unit and the second chamber is an arterial chamber placed upstream of the pump or an expansion chamber placed between the blood pump and the inlet port of the first compartment.

In a 24th aspect according to anyone of the previous aspects from 13th to 23rd, the extracorporeal blood circuit comprise a third chamber, wherein a third pressure sensor is associated to an upper portion of the third chamber.

In a 25th aspect according to the previous aspect, the control unit is configured to monitor the volume V1 of gas in the upper portion of the first chamber, the volume V2 of gas in the upper portion of the second chamber and the volume V3 of gas in the upper portion of the third chamber through said phase shift θ.

In a 26th aspect according to the previous aspect, the control unit is configured to:
measure the phase shifts θ1 of a first harmonic ω1 of the signals P1(t), P2(t) between the first and the second chamber;
measure the phase shifts θ2 of a second harmonic ω2 of the signals P1(t), P3(t) between the first and the third chamber;
measure the phase shifts θ3 of a third harmonic ω3 of the signals P3(t), P2(t) between the third and the second chamber;
calculate the volumes V1, V2, V3 of gas in the first and second chambers through:

$$\theta1=(\arctan(-\omega1*R*C1)-\arctan(-\omega1*R*C2))$$

$$\theta2=(\arctan(-\omega2*R*C1)-\arctan(-\omega2*R*C3))$$

$$\theta3=(\arctan(-\omega3*R*C3)-\arctan(-\omega3*R*C2))$$

the fluid compliances being:

$$C1=k1*V1/P1$$

$$C2=k2*V2/P2$$

$$C3=k3*V3/P3$$

In a 27th aspect according to the 25th aspect, the control unit 21 is configured to: change the angular frequency ω of the pump at three levels ωa, ωb, ωc;
measure the phase shifts θa, θb, θc at each of the three frequencies ωa, ωb, ωc;
measure the average pressures P1a, P2a, P3a, P1b, P2b, P3b, P1c, P2c, P3c in the chambers at each of the three frequencies ωa, ωb, ωc;
calculate the volumes V1a, V1b, V1c, V2a, V2b, V2c, V3a, V3b, V3c of chambers at the three frequencies ωa, ωb, ωc from the measured phase shifts θa, θb, θc.

In a 28th aspect according to the previous aspect, the volumes V1a, V1b, V2a, V2b, V3a, V3b are calculated through:

$$\theta a=(\arctan(-\omega a*R*C1a)-\arctan(-\omega a*R*C2a))$$

$$\theta b=(\arctan(-\omega b*R*C1b)-\arctan(-\omega b*R*C3b))$$

$$\theta c=(\arctan(-\omega c*R*C3c)-\arctan(-\omega c*R*C2c))$$

$$P1a*V1a=P1b*V1b=P1c*V1c$$

$$P2a*V2a=P2c*V2c=P2b*V2b$$

$$P3c*V3c=P3b*V3b=P3a*V3a$$

the fluid compliances being:

$$C1a=k1*V1a/P1a$$

$$C1b=k1*V1b/P1b$$

$$C2a=k2*V2a/P2a$$

$$C2c=k2*V2c/P2c$$

$$C3b=k3*V3b/P3b$$

$$C3c=k3*V3c/P3c$$

In a 29th aspect according to anyone of the previous aspects, the control unit is configured to calculate the level L1, L2, L3 of blood in the chamber/s starting from the volumes V1, V2, V3 of gas and the given geometry of said chambers.

In a 30th aspect according to anyone of the previous aspects, if the level L1, L2, L3 of blood and/or the volume V1, V2, V3 of air in the chamber/s is/are outside predetermined ranges, the control unit is configured to emit at least an alarm signal and/or initiate a control procedure to correct said level/s L1, L2, L3.

In a 31st aspect according to anyone of the previous aspects, the level L1, L2, L3 of blood and/or the volume V1, V2, V3 of air in the chamber/s is/are adjusted manually or automatically to keep it/them in predetermined ranges. To this aim, an air pump or an air venting valve connected to environment or pressurized chamber may be connected to the chamber/s. Said air pump or air venting valve may be controlled by the control unit.

In a 32nd aspect according to the previous aspect, the automatic adjustment is performed during priming and/or during patient treatment.

In a 33rd aspect according to the 5th aspect, the control unit is configured to allow setting of the desired phase shift θ', corresponding to the desired volume V' of gas in the upper portion of the chamber, during priming and to allow air injection into or air withdrawal from said upper portion during treatment in order to keep the measured phase shift θ at the desired phase shift θ'.

In a 34th aspect according to the previous aspect, setting of the desired phase shift θ' during priming comprises:
injecting air/gas into the chamber until a level detector senses air/gas (the geometry of the chamber and the position of the level detector are known; it follows that also the volume of gas/air in the chamber when the level detector senses air/gas is known);
removing a known volume of air/gas from the chamber in order to obtain the desired volume V' of gas in the upper portion of the chamber since the removed volume of gas is known too, the residual and desired volume V' of gas is known);
calculating the desired phase shift θ' corresponding to the desired volume V'.

In a 35th aspect according to anyone of the previous aspects, the apparatus comprises a bubble detection device; wherein the control unit is configured to calculate a relative position of the bubble detection device with respect to the venous chamber.

In a 36th aspect according to the previous aspect, the relative position of the bubble detection device is calculated by:
calculating the volume V1 of gas in the upper portion of the venous chamber;
causing injection of a predetermined volume (Vi) of air/gas in the venous chamber until the bubble detection device senses air/gas;
calculating the volume Vi of injected air/gas;
calculating a sum of the volume V1 of gas and of the volume Vi of injected air/gas;
calculating said relative position by dividing said sum by the cross sectional area of the venous chamber.

This position is important in relation to the actual blood level of the venous chamber, since it determines the risk for air reaching the patient.

This is a useful feature in particular for apparatuses in which the venous chamber can be placed differently with respect to the air bubble sensor.

In a 37th aspect according to anyone of the previous aspects, the apparatus comprises a treatment fluid circuit, wherein the second compartment is part of said treatment fluid circuit and valves in the treatment fluid circuit are closed when the control unit receives from the first pressure sensor and from the second pressure sensor and, if present, from the third pressure sensor signals P1(t), P2(t), P3(t) relating to at least one pulse of pressure of the blood flow. This allows not to loose pulse energy through the treatment fluid circuit and to increase the magnitude of the blood pulses.

In a 38th aspect according to anyone of the previous aspects, comprising an actuator in the extracorporeal blood circuit, such as a cyclically activated clamp, configured for generating the pulse of pressure.

In a 39th aspect according to anyone of the previous aspects, wherein the blood pump is controlled by the control unit for generating the pulse of pressure.

In a 40th aspect according to anyone of the previous aspects, the control unit is connected with the blood pump and configured such as to move the blood pump to generate a variable blood flow comprising a constant flow component of a set blood flow value and a variable flow component having a substantially nil average value, the variable blood flow generating a plurality of pulses of pressure. The pulsation generated by the working cycle of the blood pump to make the blood flowing is enough to detect the volume/s of air according to the present invention. No further and independent pulse generator is needed.

In a 41st aspect according to anyone of the previous aspects from 1st to 35th, the apparatus comprises a treatment fluid circuit, wherein the second compartment is part of said treatment fluid circuit and the pulse of pressure is induced in the blood flow by pulses of the fluid in the treatment fluid circuit. Pressure pulses generated on the dialysate side may be used as an alternative to the blood pump.

In a 42nd aspect according to the previous aspect, the pulse of pressure is generated by an actuator, such as a cyclically activated clamp, in the treatment fluid circuit.

In a 43rd aspect according to the previous aspect, the pulse of pressure is generated by pump in the treatment fluid circuit.

DESCRIPTION OF THE DRAWINGS

Some drawings are provided by way of non-limiting example, related to aspects of the invention.

In particular.

DETAILED DESCRIPTION

With reference to the accompanying drawings, 1 denotes an apparatus for the extracorporeal treatment of blood. The apparatus 1 comprises an extracorporeal circuit 8 arranged to extract blood from the cardiovascular system of a subject, for example a patient M, and return the treated blood to the patient M. Examples are described hereinafter relating to the overall structure of the apparatus 1: this general description concerns the extracorporeal blood circuit, the infusion lines, if present, in which a replacement fluid may circulate, the dialysis line, if present, in which a dialysis fluid may circulate, and the waste fluid discharge line.

Figure 1:
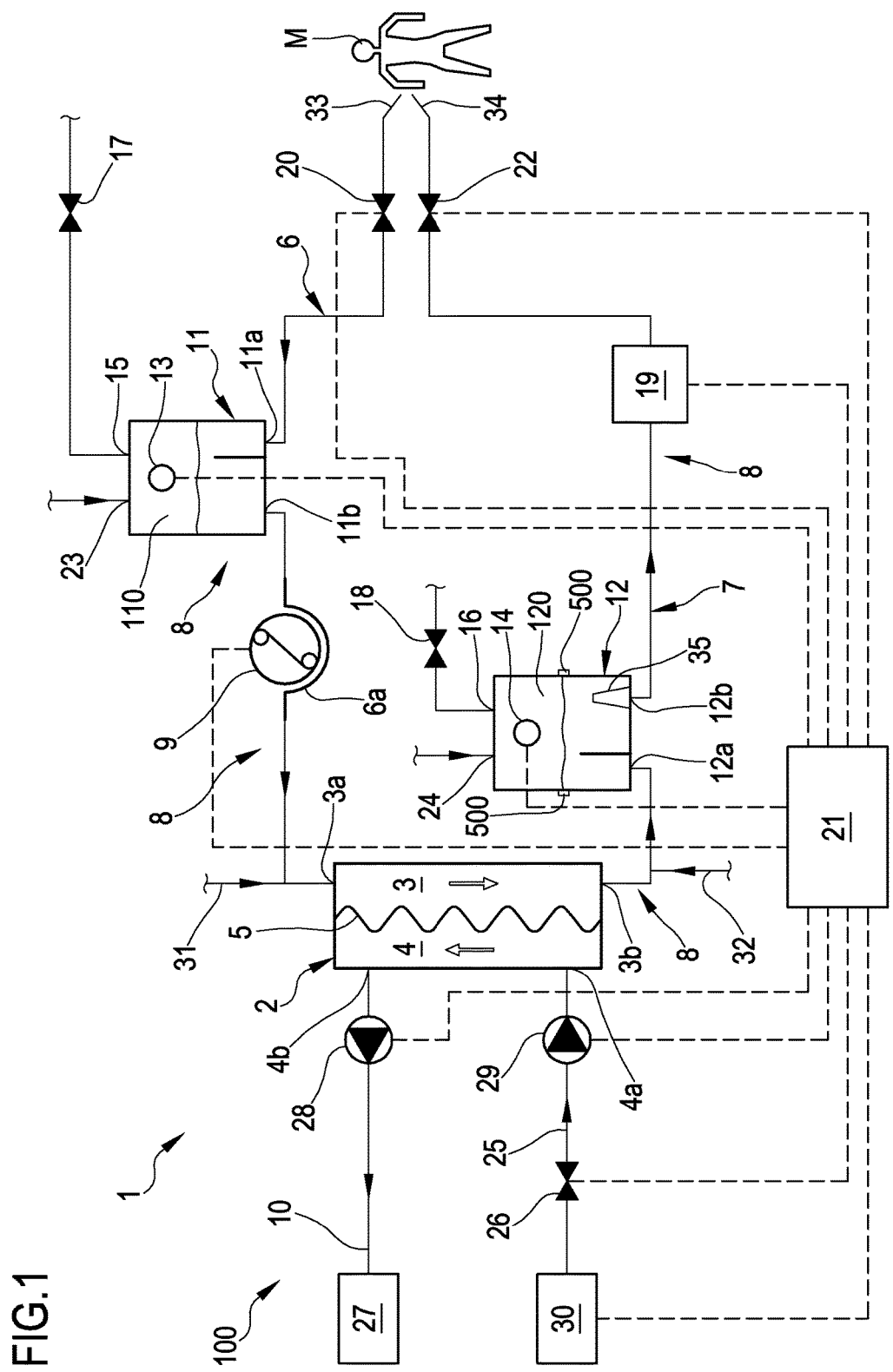
FIG. 1 schematically shows a blood treatment apparatus, according to aspects of the invention.

With reference to FIG. 1, the apparatus for the extracorporeal treatment of blood 1 comprises at least one treatment unit 2, for example a hemofilter, a hemodiafilter, a plasmafilter, a dialysis filter, a membrane oxygenator or other unit suitable for processing the blood taken from the patient M. The treatment unit 2 has at least a first compartment 3 and at least a second compartment 4 separated from one another by a semipermeable membrane 5. A blood removal line 6 is connected to an inlet port 3a of the first compartment 3 and is configured, in an operative condition of connection to the patient M, to remove blood from a vascular access device inserted, for example in a fistula on the patient M. A blood return line 7 connected to an outlet port 3b of the first compartment 3 is configured to receive treated blood from the treatment unit 2 and to return the treated blood, e.g. to a further vascular access also connected to the fistula of the patient M. Note that various configurations for the vascular access device may be envisaged: for example, typical access devices include a needle or catheter inserted into a vascular access which could be a fistula, a graft or a central (e.g. jugular vein) or peripheral vein (femoral vein) and so on.

As shown in FIG. 1, the apparatus 1 comprises at least a first actuator 9, in the present example a blood pump 9, which operates at the blood removal line 6, to cause movement of the blood removed from the patient M from a first end 33 of the removal line 6 connected to the patient M to the first compartment 3. The blood pump 9 is, for example, a peristaltic pump, as shown in FIG. 1, that acts on a respective tube pump section 6a. When rotated, e.g., clockwise-, the blood pump 9 causes a flow of blood along the blood removal line 6 towards the first compartment 3 (see the arrows in FIG. 1 indicative of the blood flow along the blood removal line 6).

It should be noted that for the purposes of the present description and the appended claims, the terms "upstream" and "downstream" may be used with reference to the relative positions taken by components belonging to or operating on the extracorporeal circuit. These terms are to be understood with reference to a blood flow direction from the first end 33 of the blood removal line 6 connected to the patient M towards the first compartment 3 and then from the first compartment 3 towards a second end 34 of the blood return line 7 connected to the vascular access of the patient M.

In the example of FIG. 1, the extracorporeal circuit comprises at least one arterial chamber 11 on the arterial blood removal line 6 from the patient M. The arterial chamber 11 is arranged upstream with respect to the first compartment 3 and—more specifically—upstream with respect to the blood pump 9. The arterial chamber 11 receives blood directly from the patient M and is configured to accumulate a set amount of blood that will remain substantially constant throughout the treatment, as it will be further explained herein below. The extracorporeal circuit also comprises at least one venous chamber 12 which operates on the venous blood return line 7, downstream of the first compartment 3 and upstream of the vascular access that returns treated blood to the patient M. In practice, the blood removal line 6, the arterial chamber 11, the first compartment 3 of the treatment unit 2, the return line 7 of the blood to the patient M and the venous chamber 12 are part of the extracorporeal blood circuit 8, which, during use of the apparatus 1, provides for the circulation of blood externally of the body of the patient M undergoing treatment.

In accordance with an aspect, at least one, and optionally both of the arterial and venous chambers 11, 12 have a constant containment volume. That is, the chambers 11, 12 are made of a rigid and substantially non-deformable material (at least in connection with the pressure regimen typically present during blood treatment).

A first pressure sensor 14 is configured to detect at least a parameter relating to the pressure of the fluid present in the venous chamber 12 and a second pressure sensor 13 is configured to detect at least a parameter relating to the pressure of the fluid present in the arterial chamber 11. The sensors 13, 14 are configured to generate a respective signal corresponding to a measured value of the parameter, which is then fed to a control unit 21. More specifically, either the control unit 21 may be configured to activate and/or poll the sensors 13 and 14, at successive instants, each time a measurement is required, or the sensors 13, 14 are configured to carry out measurements at successive instants of time. In the embodiment shown in FIG. 1, the pressure sensors 13, 14 are positioned in the corresponding arterial and venous chambers 11; 12 at upper portions 110, 120 thereof where, in use, it is expected that a gas (air) is present.

The arterial and the venous chambers 11, 12 are substantially arranged such that—in use and during blood treatment—they each accommodate a predetermined amount of gas in an upper portion 110, 120 and a predetermined amount of blood (up to a predetermined level) in a lower portion thereof. Each of the arterial and venous chambers 11, 12 has a respective inlet 11a, 12a for receiving incoming blood. The inlet 11a to the arterial chamber 11 is in fluid connection with a first part of the blood removal line 6 connected to the vascular access of the patient M, while the inlet 12a to the venous chamber 12 is in fluid connection with the blood return line 7 portion downstream the treatment unit 2. Inlets 11a, 12a may be positioned at a base portion 610, 620 of the corresponding arterial and venous chamber 11, 12. The inlets 11a and 12a are arranged such that, in use, they are directed vertically and always filled with blood.

In an embodiment, one or both of the inlets 11a, 12a may be connected to a respective channel 700, 800 formed internally of the respective arterial and/or venous chamber 11, 12. This channel 700, 800 extends—with reference to a use condition—vertically in the respective chamber and an outlet is located in the chamber at a height with respect to the base 610, 620.

Each of the arterial and venous chambers 11, 12 also includes a respective outlet 11b, 12b for the outflowing blood. Each outlet 11b, 12b is in fluid connection with the extracorporeal circuit 8 respectively at the blood removal line 6 and at the blood return line 7. The outlets 11b, 12b are positioned at the base portion 610, 620 respectively of the arterial and venous chamber 11; 12 and are arranged such that, in use, they are directed vertically and always filled with blood.

The portion of the removal line 6 which connects the outlet 11b of the arterial chamber 11 to the first compartment 3 of the treatment unit 2 comprises the tube pump section 6a which—in use—is engaged by the peristaltic pump 9. The peristaltic pump 9 is configured for sequentially squeezing the same tract of tube to thereby move the blood in the extracorporeal circuit 8. A particular type of peristaltic pump 9 may be provided with two (or more) squeezing bodies (e.g., in the form of rollers) that act on the tube pump section 6a twice (or more times) per turn of the blood pump 9.

The venous chamber 12 may internally house a venous filter 35 which separates the outlet 12b from the remaining volume of the chamber 12. The venous filter 35, for instance comprising a net structure located at the outlet 12b, helps avoiding air bubbles reaching the patient because it brakes bigger air bubbles down into smaller air bubbles which are then trapped in the venous chamber 12 and vented. Each of the venous and arterial chambers 11, 12 has also a vent opening or a vent line 15, 16 configured to allow, in use, a communication of gas between the arterial and venous and the external environments.

The apparatus 1 further comprises at least one actuator 17, 18 for each chamber 11, 12 operating on the vent opening or vent line 15; 16 for selectively inhibiting or enabling the passage of gas. The vent opening or line 15; 16 may be positioned at an upper portion of the arterial and venous chamber 11; 12. With reference to a use condition the vent opening 15, 16 may be configured to face upward, and is intended to be always in contact with gas. The actuator 17; 18 may be an air pump or a clamp (or other occluding device). The actuator 17, 18 may be controlled (or not) by the control unit 21 for allowing gas venting should it be required.

Each of the arterial and venous chambers 11, 12 may also possibly include a further access 23, 24 (service access) for receiving further fluids, medicaments or other substances in the chamber.

In relation to the set level of blood in the arterial and venous chambers 11, 12, it should be noted that—in general—this level should be within a predetermined range between a minimum value and a maximum value; in general the minimum value and a maximum value for the venous chamber 12 are different from the maximum and minimum levels for the arterial chamber 11. When the blood level is kept within these maximum and minimum values in the respective chamber, it may be assumed that the equipment is working in a safe state. When on the other hand blood level moves below the minimum value or above the maximum value, various problems may arise, as described in the following.

The apparatus 1 further comprises a first fluid flow intercept device 20 operating on the blood removal line 6 upstream of the blood pump 9 and the arterial chamber 11 and at least a second fluid flow intercept device 22 operating in the blood return line 7 downstream of the venous chamber 12. The intercept devices 20, 22, which may for example each comprise a respective clamp controlled by the control unit 21, are arranged in the vicinity of the first and second patient ends 33, 34 of the respective lines.

The apparatus 1 may also include an air-bubble sensor 19 connected to the control unit 21 and capable of generating a signal that, if above a threshold, determines the generation of a closing command of the intercept device 22 and shuts down the blood pump 9. In practice, either the air-bubble sensor 19 is configured to issue the signal to the control unit 21 only when a bubble above a certain size is detected, or the air-bubble sensor 19 communicates constantly (or at short time intervals) a signal. In the latter case, the control unit 21 is configured to read the signal and to intervene with the generation of the closing command and the blood pump shut down when the signal passes a certain threshold. In particular the air-bubble sensor 19 is located on the blood return line 7, and more particularly, downstream of the venous chamber 12 along the blood flow direction in the extracorporeal circuit 8.

The apparatus 1 further comprises at least one fluid evacuation line 10 connected with an outlet port 4b of the second compartment 4 such as to receive at least a filtered fluid through the semipermeable membrane 5. The evacuation line 10 receives the waste fluid coming from the second compartment 4 of the treatment unit 2, for example, comprising used dialysis liquid and/or liquid ultra-filtered through the membrane 5. The evacuation line 10 leads to a receiving element 27, for example having a collection bag or a drainage pipe for the waste fluid. One or more dialysate pumps 28 may operate on the evacuation line 10.

For example in the accompanying FIG. 1, a pump 28 active on the evacuation line 10 is provided. Note that the structure of the evacuation line may also be different from the one illustrated (as long as it may properly drain fluid exiting from the second compartment 4): for example the evacuation line 10 may comprise a single line as shown in the accompanying figure or a main drainage line and an ultrafiltration line branching off the main discharge line and provided with a respective ultrafiltration pump (this solution not shown in the drawings).

In the example of FIG. 1, a dialysis line 25 is also present, for supplying a fresh treatment fluid to an inlet port 4a of the second compartment 4. The presence of this line is not strictly necessary since, in the absence of the dialysis line 25, the apparatus 1 is still able to perform treatments such as ultrafiltration, hemofiltration or plasmafiltration. In case the dialysis line 25 is present, a third fluid flow intercept device 26 may be used to selectively allow or inhibit fluid passage through the dialysis line 25, depending on whether or not a purification by diffusive effect is to be performed inside the treatment unit 2.

The dialysis line 25, if present, is typically equipped with a dialysis pump 29 and is able to receive a fresh fluid from a module 30, for example a bag or on-line preparation section of dialysis fluid, and to send such a fluid to the inlet port 4a of the second compartment 4. The fluid evacuation line 10, the dialysis line 25, and the second compartment 4 are part of a treatment fluid circuit, globally indicated with reference number 100 in the accompanying drawings.

Finally, the apparatus 1 may comprise one or more infusion lines of a replacement fluid: for example a pre-infusion line 31 may be connected to the blood removal line 6 and/or a post-infusion line 32 may be connected to the blood return line 7. The pre- and/or post-infusion lines 31, 32 may be supplied by fluid coming from bags or directly by infusion fluid prepared on-line, e.g. using module 30. These lines are only schematically represented in the accompanying figures as they are per se known.

The control unit 21 of the apparatus 1 may comprise one or more digital modules, for example of the microprocessor type, or one or more analog modules, or a suitable combination of digital and analog modules. As illustrated in the example of FIG. 1, the control unit 21 is connected with the blood pump 9 and/or with the dialysate pump 28 and/or with the dialysis pump 29, as well as with the first and second pressure sensors 13, 14 located at the arterial and venous chambers 11, 12 and optionally, if present, with auxiliary pressure sensors. In addition, the control unit 21 may be connected to the first and second fluid flow intercept devices 20, 22 and, if present, to the third fluid flow intercept device 26. The control unit 21 is also in communication with the bubble detection device 19, with the module 30 (if the preparation is on-line) and possibly with the actuators 17, 18 on the vent openings/lines 15, 16. The control unit 21 is configured or programmed to perform the procedures described below.

If the control unit 21 is of the programmable type, this unit is connected with a data carrier for storing instructions that, when performed by the control unit 21, carry out the procedures described below. The data carrier may comprise a mass storage, for example, optical or magnetic, a re-programmable memory (EPROM, FLASH) or a memory of another type.

In general, before a treatment is started, the apparatus 1 is subjected to a priming procedure controlled by the control unit 21. In particular, prior to treatment, a saline solution is fed into the extracorporeal circuit 8 to wash and remove any air and residual particles from the blood line and from the treatment unit. At the end of this procedure, a set level of saline at the working pressure is established in the arterial and venous chambers 11, 12.

Once the patient M is connected to the equipment via the vascular access, the control unit 21 is configured to move at least the blood pump 9 to create, in the arterial and venous chambers 11, 12, a corresponding set blood level in the lower portion of each chamber, while confining a complementary quantity of gas in the upper portion of each chamber. The treatment at this point may start and continue for the duration required in order to appropriately treat the blood taken from the patient M.

Throughout the treatment, the blood level in the arterial and venous chambers 11, 12 continuously changes (although by small amounts) at least as a result of the fact that the control unit 21 moves the blood pump 9 and generates a variable flow of blood comprising a constant flow component equal to a desired blood flow value and a variable flow component at substantially zero average value. This is due in particular to the fact that the blood pump 9 is peristaltic in nature and therefore produces a non-constant flow of blood in the circuit, caused by the successive squeezing actions of the tube pump section 6a operated by the roller/rollers associated to the pump rotor.

In other words, the hydraulic pressure of the blood pumped in the extracorporeal circuit is given by a tube constriction (generated by the pump roller in contact with pump segment 6a) which runs along the tube segment 6a. In the described example, the pump 9 comprises a rotor with two (or more) rollers, which upon rotation of the pump rotor "squeeze" the tube segment 6a and cause the advancement of the fluid in the blood circuit.

Alternatively to what has been described, other types of 'peristaltic' pumps may be used capable of generating a non-constant flow comprising an average constant component and a variable zero average component. For instance, linear peristaltic pumps may be used (for example, "finger" pumps) or cyclically activated pumps, or clamps capable of generating a pulsating movement in the blood.

Alternatively, the control unit 21 may be configured to control the pump 9 to generate the pulsating movement in the blood in order to use other kinds of pumps which do not have inherently generated pressure variations. Alternatively, the control unit 21 might control an actuator, such as a cyclically activated clamp (as the third fluid flow intercept device 26) or another pump (as the dialysate pumps 28 or the dialysis pump 29), in the treatment fluid circuit 100 which is configured to induce pulses of pressure in the blood flowing in the extracorporeal blood circuit 8.

Irrespective of how it is created, the variable blood flow generates in both the arterial and venous chambers 11, 12 a time-variable pressure function P(t) comprising a pressure component ΔP(t) oscillating about an average pressure value Pavg. When the pump 9 or other actuators generates the pulsating movement, valves 26 in the treatment fluid circuit 100 may be closed to increase the magnitude of the blood pulses.

The control unit 21 is configured to monitor volumes V1, V2 of gas/air in the upper portions 120, 110 of the venous and arterial chambers 12, 11.

For instance, the control unit 21 is configured to calculate the volumes V1, V2 of gas/air (and, in case, the amounts of gas in mol) in the upper portions 120, 110 of the venous and arterial chambers 12, 11 and, from these volumes V1, V2 (and from the known geometry of said chambers 12, 11), levels L1, L2 of blood in such chambers 12, 11. This allows detecting variations of the blood levels L1, L2 in the chambers 11, 12 and thus helps reducing the risk of infusing bubbles of gas into a patient.

For this purpose, the control unit 21 receives from the first pressure sensor 14 and from the second pressure sensor 13 pressure signals P1(t) and P2(t) related to the time-variable pressure P(t) generated by the blood pump 9 (or by other actuators). This time-variable pressure P(t) reaches the first pressure sensor 14 with a first time delay (with respect to its generation) mainly due to said volume V1 of gas/air in the upper portion 120 of the venous chamber 12. The time-variable pressure P(t) reaches the second pressure sensor 13 with a second time delay (with respect to its generation) mainly due to said volume V2 of gas/air in the upper portion 110 of the arterial chamber 11.

In the frequency domain, where the first time delay corresponds to a first phase shift θ1 and the second time delay corresponds to a second phase shift θ2, these phase shifts are as follows:

$$\theta_1 = \arctan(-\omega \cdot R_1 \cdot C_1)$$

$$\theta_2 = \arctan(-\omega \cdot R_2 \cdot C_2), \text{ wherein}$$

ω angular frequency of the pressure signal
R1 fluid resistance of the venous chamber
R2 fluid resistance of the arterial chamber
C1=k1*V1/P1 fluid compliance of the venous chamber
C2=k2*V2/P2 fluid compliance of the arterial chamber
P1 average pressure in the venous chamber
P2 average pressure in the arterial chamber The control unit 21 is configured to receive said pressure signals P1(t), P2(t) and calculate the difference θ=θ1−θ2 between the time delays/phase shifts:

$$\theta = (\arctan(-\omega \cdot R_1 \cdot k_1 \cdot V_1/P_1) - \arctan(-\omega \cdot R_2 \cdot k_2 \cdot V_2/P_2))$$

Figure 4A:
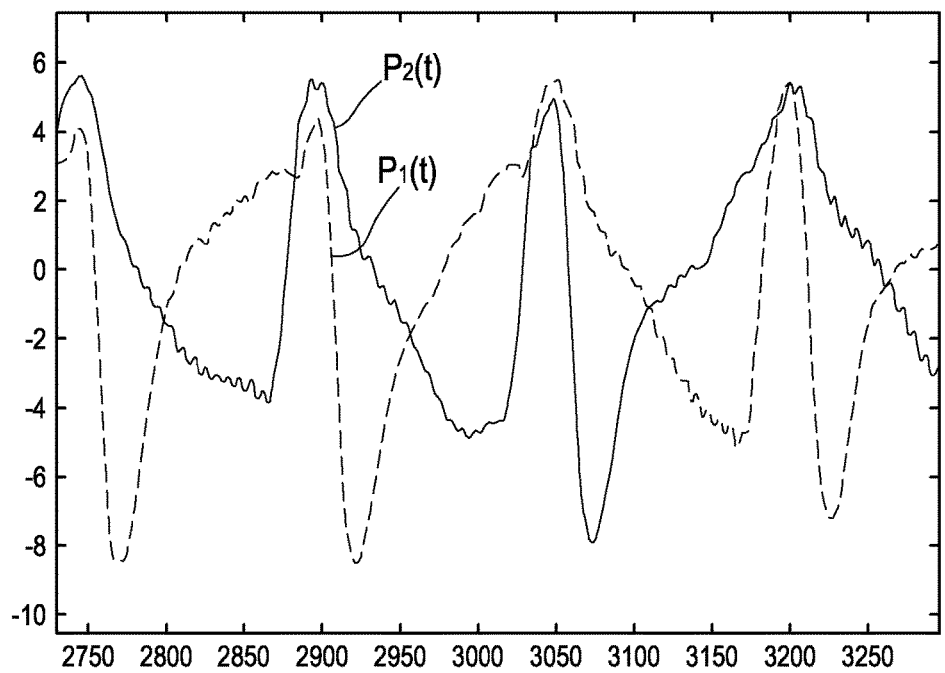
FIGS. 4a and 4b show pressure trends detected by two pressure sensors of the apparatus, for example of the type shown in FIG. 1.

After the priming procedure, the volumes V1a, V2a of gas (and the levels L1a, L2a of blood) in the venous chamber 12 (first chamber) and in the arterial chamber 11 (second chamber) are known and are basically the same. In this condition, the time variable pressure P(t) propagating through air/gas in the chambers 11, 12, reaches the first pressure sensor 14 and the second pressure sensor 13 at the same time (the first time delay is equal to the second time delay). The phase shift θ calculated by the control unit 21 is zero (if R1=R2 and k1=k2). This condition is shown in FIG. 4a in which the peaks of time-variable pressure signals P1(t)—venous pressure, P2(t)—arterial pressure generated by the two sensors (when reached by the time variable pressure P(t)) are aligned.

Figure 4B:
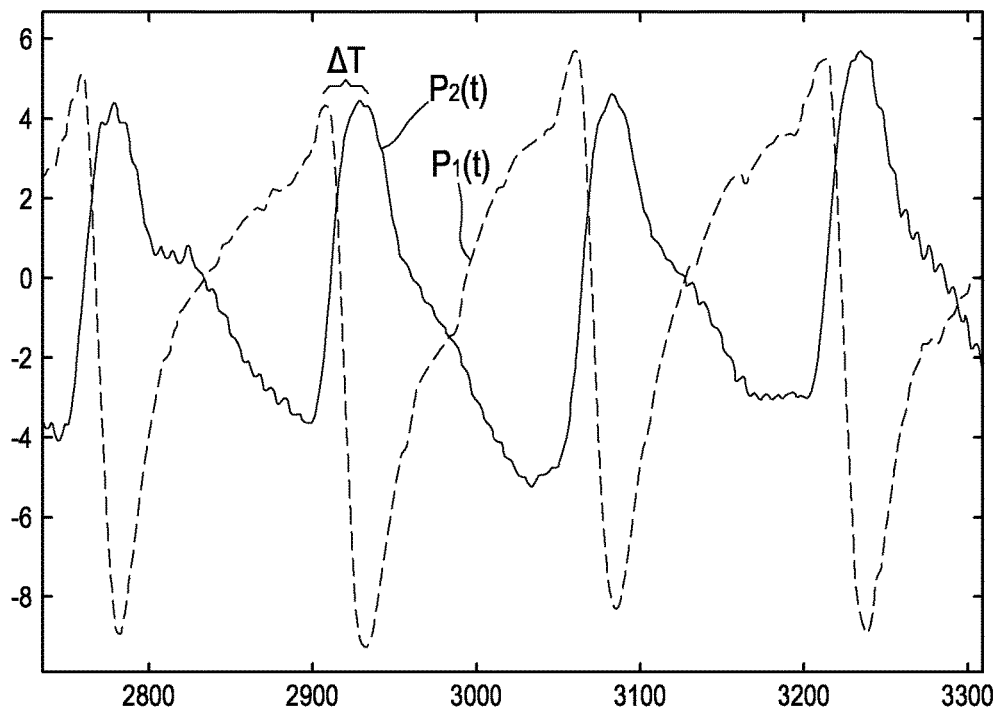

During treatment of the patient M, the volume of gas/air in the venous chamber 12 changes. This change or misalignment of "blood levels/volumes of air" in the two chambers gives rise to a time delay ΔT and the peaks of the time-variable pressure P1(t), P2(t) detected by the two sensors 14, 13 are shifted by the time delay ΔT, as shown in FIG. 4b. In FIG. 4b, the arterial pressure P2(t) presents a time delay with respect to the venous pressure P1(t) since the air/gas volume in the arterial chamber 11 (which means the compliance C2 of the arterial chamber 11) is greater than the air/gas volume in the venous chamber 12 (which means the compliance C1 of the venous chamber 12).

If, under certain conditions, during treatment of the patient M, the volume V2 of gas/air and the average pressure P2 in the arterial chamber 11 are (or can be assumed) substantially steady, the equation above allows calculating the volume V1 in the venous chamber 12:

$$V_1 = f_1(\theta, \omega, P_1, V_{2a}, P_{2a}),$$

wherein:
θ is measured;
ω is known/measured;
P1 is measured;
V2=V2a and P2=P2a is known after priming.

The function "f1" can be a function comprising experimentally-determined constants or a correlation table obtained through empirical tests.

If the volume of gas/air in the arterial chamber 11 cannot be considered steady, according to a calculating method, the control unit 21 further calculates the magnitudes of the time-variable pressure signals P1(t), P2(t), wherein the magnitudes are correlated to the fluid compliances C1 and C2 of the venous and arterial chambers 12, 11, through:

$$|P_1|/|P_2| = \sqrt{(1+(\omega \cdot R_2 \cdot C_2)^2)/(1+(\omega \cdot R_1 \cdot C_1)^2)}$$

Using:

$$\theta = (\arctan(-\omega \cdot R_1 \cdot k_1 \cdot V_1/P_1) - \arctan(-\omega \cdot R_2 \cdot k_2 \cdot V_2/P_2))$$

and $$|P_1|/|P_2| = \sqrt{(1+(\omega \cdot R_2 \cdot k_2 \cdot V_2/P_2)^2)/(1+(o \cdot R_1 \cdot k_1 \cdot V_1/P_1)^2)}$$

wherein:
θ is measured;
ω is known/measured;
P1 is measured;
P2 is measured;
|P1| is measured;
|P2| is measured.

It is then possible to calculate volumes V1 in the venous chamber 12 and volume V2 in the arterial chamber 11.

According to a different embodiment, if the volume of gas/air in the arterial chamber 11 cannot be considered steady, the control unit 21 is configured to:
  change the angular frequency ω of the pump 9 at two levels ωa, ωb;
  measure the phase shifts θa, θb at each of the two frequencies ωa, ωb;
  measure the average pressures P1a, P2a, P1b, P2b in the chambers 11, 12 at each of the two frequencies ωa, ωb;

calculate the volumes V1a, V1b, V2a, V2b of chambers 11, 12 at the two frequencies ωa, ωb from the measured phase shifts θa, θb.

If no gas/air enters or exits the chambers and the temperature does not change, the following set of equations can be solved for calculating volumes:

$$\theta a = (\arctan(-\omega a*R*C1a) - \arctan(-\omega a*R*C2a))$$

$$\theta b = (\arctan(-\omega b*R*C1b) - \arctan(-\omega b*R*C2b))$$

$$P1a*V1a = P1b*V1b$$

$$P2a*V2a = P2b*V2b,$$

wherein the fluid compliances are:

$$C1a = k1*V1a/P1a$$

$$C1b = k1*V1b/P1b$$

$$C2a = k2*V2a/P2a$$

$$C2b = k2*V2b/P2b$$

According to a further different embodiment, if the volume of gas/air in the arterial chamber 11 cannot be considered steady, the control unit 21 is configured to:
measure the phase shifts θ1 of a first harmonic of the pulses of pressure;
measure the phase shifts θ2 of a second harmonic of the pulses of pressure;
calculate the volumes V1, V2 of chambers 11, 12 from the measured phase shifts θ1, θ2 through:

$$\theta 1 = (\arctan(-\omega 1*R*C1) - \arctan(-\omega 1*R*C2))$$

$$\theta 2 = (\arctan(-\omega 2*R*C1) - \arctan(-\omega 2*R*C2))$$

where the fluid compliances are:

$$C1 = k1*V1/P1$$

$$C2 = k2*V2/P2$$

Figure 2:
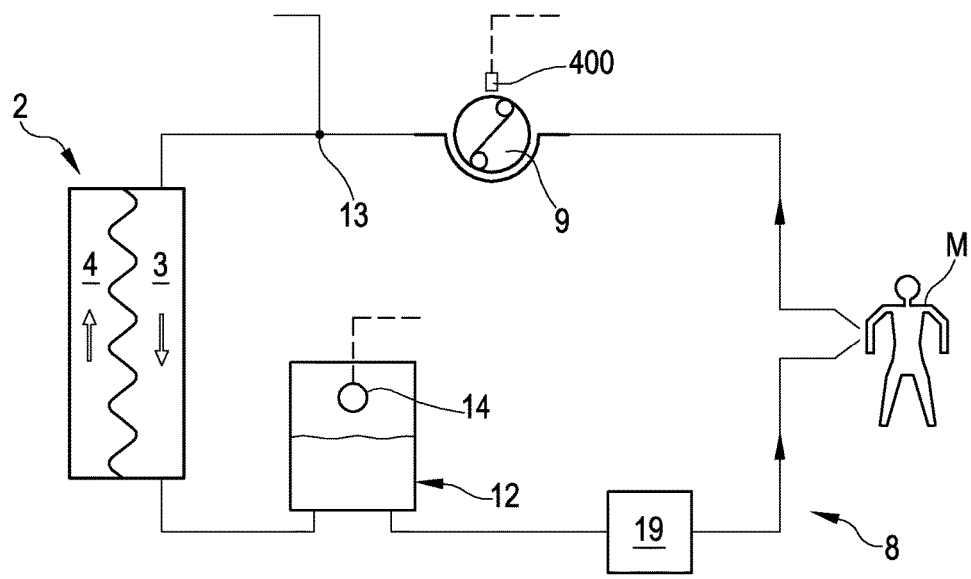
FIG. 2 shows a variant of the blood treatment apparatus of FIG. 1.

According to a different embodiment shown in FIG. 2, the apparatus 1 is not provided with the arterial chamber 11, but only the venous chamber 12 is present.

The second pressure sensor 13 is directly associated with a portion of the blood line and thus directly in contact with the blood flow. It measures the pressure signal P(t) with basically no delay with respect to the generation of the signal by the blood pump 9 (the second time delay is zero) while the first pressure sensor 14 senses the same signal of pressure in the upper portion 120 of the venous chamber 12 with the first time delay. In the illustrated embodiment, the second pressure sensor 13 is located in a section between the blood pump 9 and the first compartment 3 of the treatment unit 2.

In the frequency domain, the first time delay corresponds to a first phase shift θ1 and the second time delay is zero:

$$\theta = \theta 1 = \arctan(-\omega*R1*C1)$$

wherein the fluid compliance is:

$$C1 = k1*V1/P1$$

The control unit 21 is configured to measure the (only) phase shift θ1 and the average pressure P1 and to calculate the first volume V1.

Instead of measuring the phase shift θ1 between the first pressure sensor 14 and the second pressure sensor 13, the phase shift θ1 can be measured between the first pressure sensor 14 and a signal correlated to a timing of the speed signals of the pump. For this purpose, a proximity sensor 400 can be implemented to sense the angular speed/frequency of the peristaltic pump 9 (FIG. 2).

Figure 3:
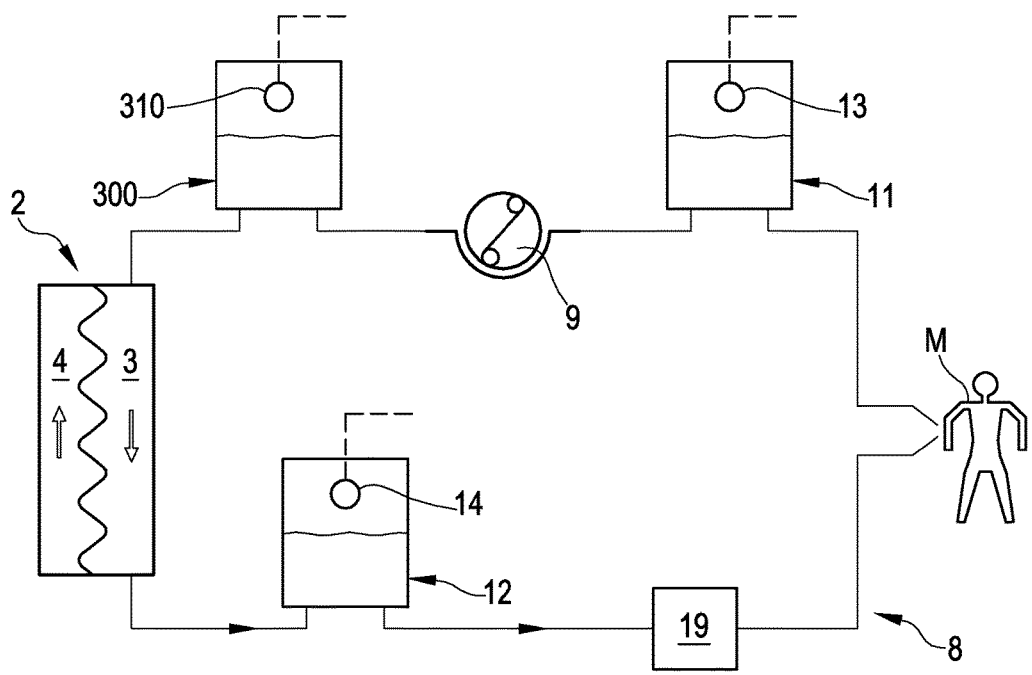
FIG. 3 shows a further variant of the blood treatment apparatus of FIG. 1.

According to a different embodiment shown in FIG. 3, the apparatus 1 comprises the arterial chamber 11, the venous chamber 12 and a further expansion chamber 300 placed between the blood pump 9 and the inlet port 3a of the first compartment 3. A third pressure sensor 310 is associated with an upper portion of the third chamber 300. The further expansion chamber 300 is implemented for enhancing the signal to noise ratio (i.e. heart vs. pump signals) in the venous chamber (for extraction of physiological pulses of the patient M conveyed by the blood line) and/or for avoiding over-pressure in the blood line after clotting of the dialyzer.

The control unit 21 is configured to calculate the air/gas volumes in the three chambers 11, 12, 300. For that purpose, according to a calculating method, the control unit 21 is configured to:
measure the phase shift θ1 of a first harmonic of the pulses of pressure between the first and the second chamber 12, 11;
measure the phase shift θ2 of a second harmonic of the pulses of pressure between the first and the third chamber 12, 300;
measure the phase shift θ3 of a third harmonic of the pulses of pressure between the third and the second chamber 300, 11;
calculate the volumes V1, V2, V3 of the chambers 11, 12, 300 with the following set of equations:

$$\theta 1 = (\arctan(-\omega 1*R*C1) - \arctan(-\omega 1*R*C2))$$

$$\theta 2 = (\arctan(-\omega 2*R*C1) - \arctan(-\omega 2*R*C3))$$

$$\theta 3 = (\arctan(-\omega 3*R*C3) - \arctan(-\omega 3*R*C2))$$

the fluid compliances being:

$$C1 = k1*V1/P1$$

$$C2 = k2*V2/P2$$

$$C3 = k3*V3/P3$$

According to a different calculating method, the control unit 21 is configured to:
set the angular frequency ω of the pump 9 at three levels ωa, ωb, ωc;
measure the phase shifts θa, θb, θc at each of the three frequencies ωa, ωb, ωc;
measure the average pressures P1a, P2a, P3a, P1b, P2b, P3b, P1c, P2c, P3c in the chambers 11, 12, 300 at each of the three frequencies ωa, ωb, ωc;
calculate the volumes V1a, V1b, V1c, V2a, V2b, V2c, V3a, V3b, V3c of chambers 11, 12, 300 at the three frequencies ωa, ωb, ωc from the measured phase shifts θa, θb, θc and from the following set of equations (if no gas/air enters or exits the chambers and the temperature does not change):

$$\theta a = (\arctan(-\omega a*R*C1a) - \arctan(-\omega a*R*C2a))$$

$$\theta b = (\arctan(-\omega b*R*C1b) - \arctan(-\omega b*R*C3b))$$

$$\theta c = (\arctan(-\omega c*R*C3c) - \arctan(-\omega c*R*C2c))$$

$$P1a*V1a = P1b*V1b = P1c*V1c$$

$$P2a*V2a = P2c*V2c = P2b*V2b$$

$$P3c*V3c = P3b*V3b = P3a*V3a$$

the fluid compliances being:

$$C1a = k1 * V1a/P1a$$

$$C1b = k1 * V1b/P1b$$

$$C2a = k2 * V2a/P2a$$

$$C2c = k2 * V2c/P2c$$

$$C3b = k3 * V3b/P3b$$

$$C3c = k3 * V3c/P3c$$

Figure 5:
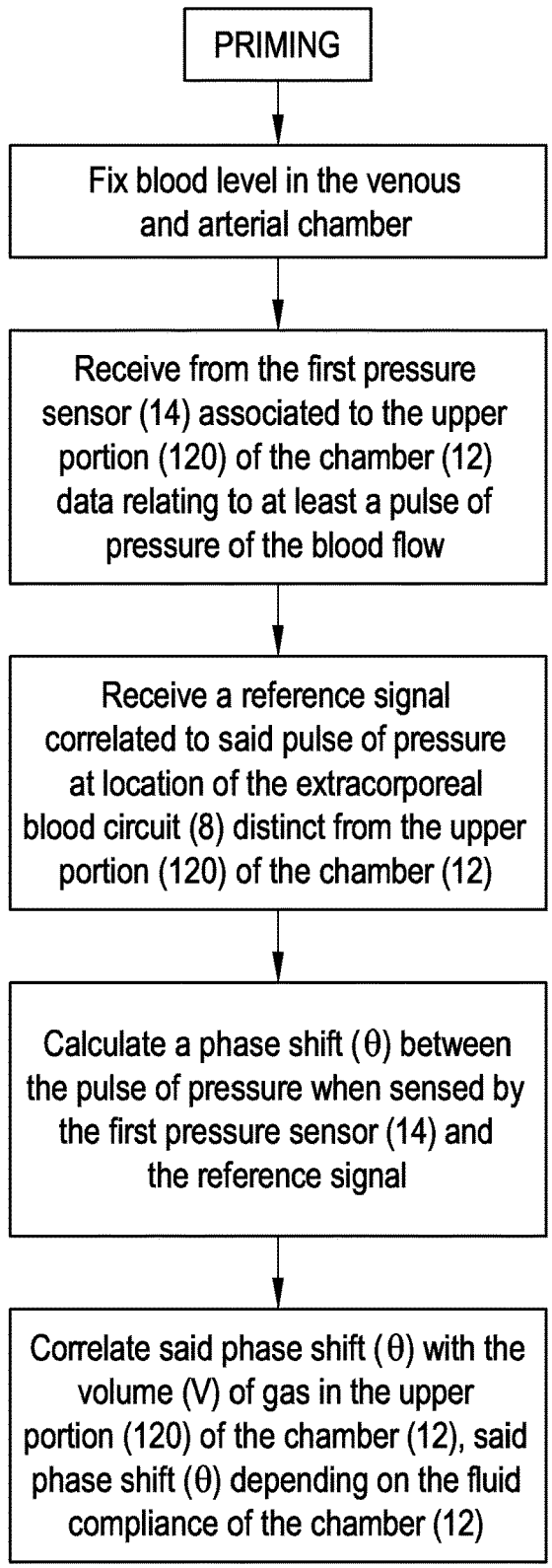
FIG. 5 is a flowchart showing a control procedure according to an aspect of the invention, performable by a control unit of an apparatus, for example of the type shown in FIG. 1.
Figure 6:
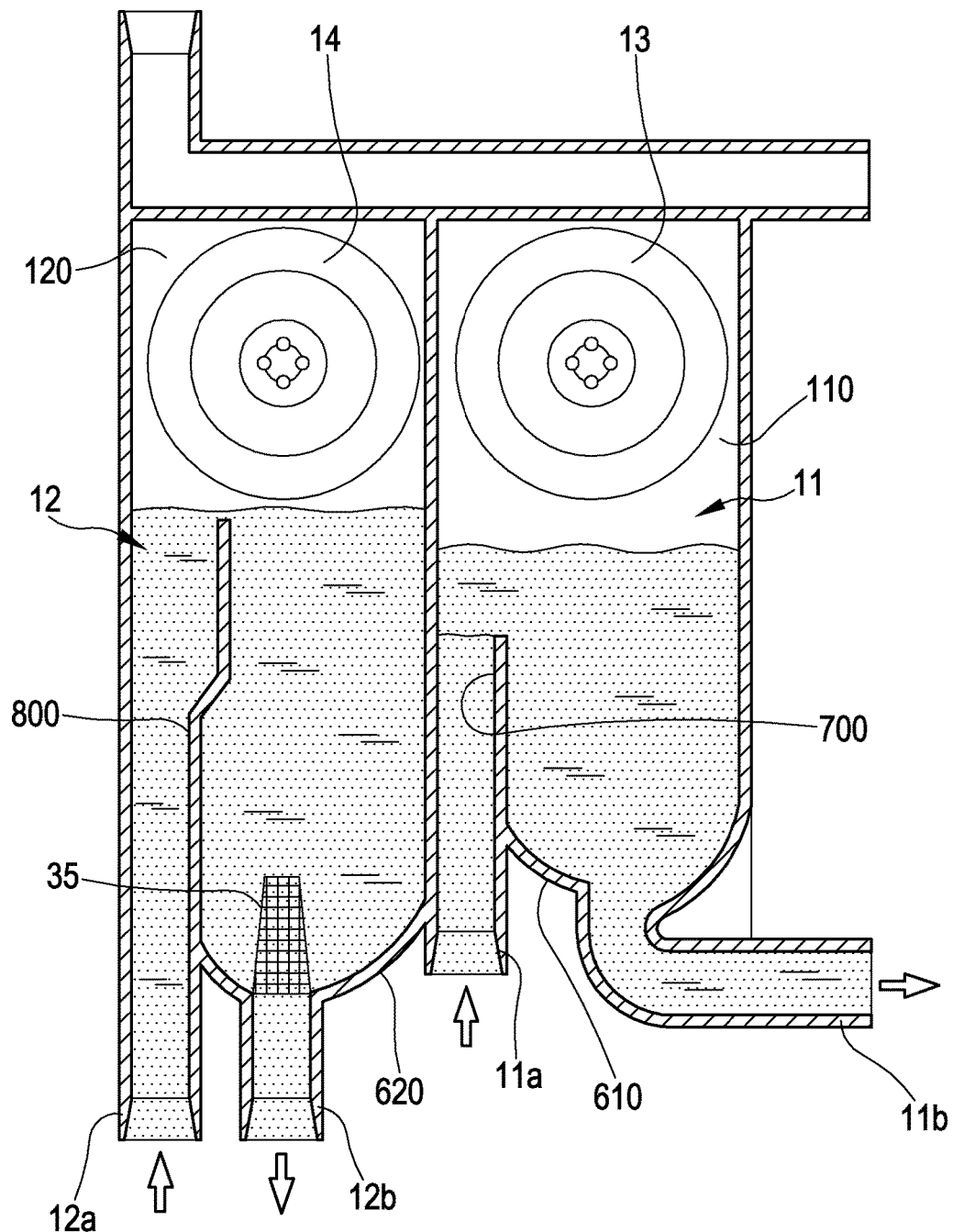
FIG. 6 shows a detail of the venous and arterial chambers of the apparatus of FIG. 1 or 3.

In all above embodiments, the control unit 21 acquires at least a pressure signal, calculates at least a time delay/phase shift and further calculates, from the phase shift, at least a volume of air/gas of at least a chamber. A flow chart of a control procedure according to an aspect of the invention, performable by the control unit 21, is shown in FIG. 5.

Apart from the specific embodiments and of the methods of calculation above illustrated, the calculated volumes V1, V2, V3, can be used to monitor and adjust the levels L1, L2, L3 of blood inside the chambers 11, 12, 300, during priming and/or during patient M treatment, in order to keep them within predetermined range/s and/or at a predetermined level/s. The control unit 21 may be configured to emit at least an alarm signal to allow a manual adjustment and/or to initiate a control procedure to correct the level/s. In this regard, an air pump can be connected to the chambers 11, 12, 300 and controlled by the control unit 21 to pump air inside the chambers, when necessary.

The calculated volume V1 of the venous chamber 12 may be used by the control unit 21 to calculate the position of the chamber 12 with respect to the air bubble sensor 19. The volume V1 of gas in the upper portion 120 of the venous chamber 12 is first calculated. Then, air/gas is injected in the venous chamber 12 until the bubble detection device 19 senses said air/gas. Then, the volume Vi of injected air/gas is calculated. The relative position is determined by dividing the sum of the volume V1 of gas and of the volume Vi of injected air/gas by the cross sectional area (which may be assumed to be constant over the height of the chamber or may be calibrated for the actual profile of the chamber) of the venous chamber 12. This procedure is conducted at the end of priming to avoid injecting air into the patient.

According to an embodiment, the control unit 21 of the apparatus 1 may be configured to adjust the levels L3, L1 of blood inside the expansion chamber 300 and the venous chamber 12 in order to minimize the air/gas volume in the venous chamber 12 and maximize the air/gas volume in the expansion chamber 300. In this way, the ripple from the blood pump will be minimized in the second pressure sensor and the heart signal will be maximized. This allows to supervise and detect a venous needle dislodgement (VNM with stethoscope method as is disclosed e.g. in WO 2009/156174) with improved accuracy and robustness and allows to minimize the number of bubbles reaching the patient.

According to an embodiment, the control unit 21 may be configured to determine, during priming, a desired phase shift $\theta'$ which is intended to be used as a reference point during treatment.

The desired phase shift $\theta'$ is set by:
injecting air/gas into the chamber 12 until a level detector 500 senses air/gas;
removing a known volume of air/gas from the chamber 12 in order to obtain the desired volume V' of gas in the upper portion 120 of the chamber 12;
calculating the desired phase shift $\theta'$ corresponding to the desired volume V'.

Since the geometry of the chamber 12 and the position of the level detector 500 are known, also the volume of gas/air in the chamber 12 when the level detector 500 senses air/gas is known. Since the removed volume of gas is known too, the residual and desired volume V' of gas is known.

The volume V of gas in the upper portion 120 of the chamber 12 is adjusted, manually or automatically with an air pump, during treatment in order to keep the measured phase shift $\theta$ at the desired phase shift $\theta'$.

Note that it may be useful to convert the achieved set-value (desired phase shift $\theta'$) obtained during priming according to a pre-defined table/function before it is used as a set-value during treatment. This is due to the following reasons. The flow resistance R of the mechanical filter would be lower when dialysis solution is used compared to when blood is used, since the viscosity of blood is substantially higher. This may change the filtering of pump pulses so that the magnitude/phase shift will change.

Since no needle is connected during priming the average pressure of the chamber 12 would become different (likely lower) during priming than during treatment. This means that the compliance of the gas in chamber 12 would be different in the two modes for the same blood flow and the filtering would become different. The conversion function/table may be based on pre-determined data at different average blood pressure with blood and with dialysis solution. The set-value for a particular blood flow and at the present average blood pressure may then be generated from the table/function. The procedure above may alternatively be performed intermittently during treatment.

Another way of implementing the method would be to remove air from the chamber to a level where the magnitude/phase shift of the pulses obtains a desired level. This level may either be fixed, or it may have a fixed relation to the pulse obtained when the gas level is at the air detector.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

The invention claimed is:

1. An apparatus for extracorporeal blood treatment comprising:
   at least one treatment unit comprising at least a first compartment;
   at least one blood removal line in fluid communication with the first compartment and configured to remove blood from a patient;
   at least one blood return line in fluid communication with the first compartment and configured to return treated blood to the patient;
   the blood removal line, the blood return line and the first compartment being part of an extracorporeal blood circuit;
   at least one chamber placed in the extracorporeal blood circuit, the chamber being arranged in use to contain a volume of gas in an upper portion and blood at a level in a lower portion;

at least one blood pump operating with the extracorporeal blood circuit and configured to move blood in the circuit;

at least a first pressure sensor associated with the upper portion of the chamber and configured to enable pressure values internally of the upper portion to be determined; and a control unit operably connected to the first pressure sensor and the pump, the control unit configured to:
receive from the first pressure sensor a first signal relating to at least one pulse of pressure of the blood flow;
calculate a phase shift between the first signal and a reference signal correlated to said at least one pulse of pressure detected at a location distinct from the upper portion of the chamber, said phase shift depending on the volume of gas in the upper portion of the chamber;
monitor said volume of gas using said phase shift; and
emit an alarm signal and/or initiate a control procedure if the volume of gas is determined to be outside a predetermined threshold.

2. The apparatus according to claim 1, wherein the reference signal is related to a timing of a control signal of the blood pump or a timing of a speed signal of the blood pump.

3. The apparatus according to claim 1, wherein the reference signal is a pressure signal of a second pressure sensor associated with the extracorporeal blood circuit.

4. The apparatus according to claim 1, wherein the at least one chamber is a venous chamber placed downstream of the treatment unit.

5. The apparatus according to claim 3, wherein the extracorporeal blood circuit comprises a first chamber and a second chamber, wherein the first pressure sensor is associated with the upper portion of the first chamber and the second pressure sensor is associated with an upper portion of the second chamber, and wherein the control unit is configured to monitor the volume of gas in the upper portion of the first chamber and the volume of gas in the upper portion of the second chamber through said phase shift.

6. The apparatus according to claim 5, wherein the control unit is configured to calculate magnitudes of pressure signals taken in the chambers and to calculate the volume of gas in the upper portion of the first chamber and the volume of gas in the upper portion of the second chamber using the phase shift and the magnitudes.

7. The apparatus according to claim 5, wherein the control unit is configured to:
set an angular frequency of the pump at a first level;
measure a first value of said phase shift at the first frequency level;
set the angular frequency of the pump at a second level;
measure a second value of said phase shift at the second frequency level;
measure average pressures in the first and second chambers at each of the two frequency levels; and
calculate the volumes of gas in the first and second chambers at the two frequency levels from the measured values of phase shift and by applying the ideal gas law.

8. The apparatus according to claim 5, wherein the control unit is configured to:
measure the phase shifts of a first harmonic of the signals;
measure the phase shifts of a second harmonic of the signals;
calculate the volumes of gas in the first and second chambers from the measured first and second harmonic phase shifts.

9. The apparatus according to claim 1, wherein monitoring the volume of gas in the upper portion of the at least one chamber includes calculating the volume of gas in the upper portion of the chamber from said phase shift.

10. The apparatus according to claim 1, wherein monitoring the volume of gas in the upper portion of the chamber comprises:
setting a desired phase shift corresponding to a desired volume of gas in the upper portion of the chamber; and
comparing the calculated phase shift, corresponding to the volume of gas in the upper portion of the chamber, with the desired phase shift.

11. The apparatus according to claim 10, wherein the control unit is configured to allow setting of the desired phase shift during priming and to allow air injection into or air withdrawal from said upper portion during treatment to maintain the measured phase shift at the desired phase shift.

12. The apparatus according to claim 1, comprising a bubble detection device, wherein the at least one chamber is a venous chamber and the control unit is configured to calculate a relative position of the bubble detection device with respect to said venous chamber.

13. The apparatus according to claim 12, wherein the relative position of the bubble detection device is calculated by:
calculating the volume of gas in the upper portion of the venous chamber;
causing injection of a predetermined volume of air/gas in the venous chamber until the bubble detection device senses air/gas;
calculating the volume of injected air/gas;
calculating a sum of the volume of gas and of the volume of injected air/gas; and
calculating said relative position by dividing said sum by the cross sectional area of the venous chamber.

14. The apparatus according to claim 1, comprising an actuator in the extracorporeal blood circuit configured for generating the at least one pulse of pressure.

15. The apparatus according to claim 1, wherein the blood pump is controlled by the control unit to generate the at least one pulse of pressure.

16. The apparatus according to claim 3, wherein the second pressure sensor is associated directly to the blood flow.

17. The apparatus according to claim 1, which includes a treatment fluid circuit, and wherein the reference signal is a pressure signal of a second pressure sensor associated with the treatment fluid circuit.

18. The apparatus according to claim 5, wherein the control unit is configured to calculate the volume of gas in the upper portion of the first chamber and the volume of gas in the upper portion of the second chamber from the phase shift, average pressures and magnitudes of said pressures.

19. The apparatus according to claim 5, wherein the first chamber is a venous chamber placed downstream of the treatment unit and the second chamber is an arterial chamber placed upstream of (i) the blood pump or (ii) an expansion chamber placed between the blood pump and an inlet port of the first compartment.

20. The apparatus according to claim 5, wherein the extracorporeal blood circuit includes a third chamber, wherein a third pressure sensor is associated to an upper portion of the third chamber.

21. The apparatus according to claim 20, wherein the control unit is configured to monitor the volume of gas in the upper portion of the first chamber, the volume of gas in the upper portion of the second chamber and a volume of gas in the upper portion of the third chamber using said phase shift.

22. The apparatus according to claim 11, wherein the setting of the desired phase shift during priming comprises:
- injecting air/gas into the chamber until a level detector senses air/gas;
- removing a known volume of air/gas from the chamber to obtain the desired volume of gas in the upper portion of the chamber; and
- calculating the desired phase shift corresponding to the desired volume.

23. The apparatus according to claim 1, comprising a treatment fluid circuit, wherein the second compartment is part of said treatment fluid circuit and valves in the treatment fluid circuit are closed when the control unit receives from said at least first pressure sensor the first signal relating to at least one pulse of pressure of the blood flow.

24. The apparatus according to claim 1, comprising a treatment fluid circuit, wherein the second compartment is part of said treatment fluid circuit, and wherein the at least one pulse of pressure is induced in the blood flow by pulses generated in the fluid of the treatment fluid circuit.

25. The apparatus according to claim 24, wherein the at least one pulse of pressure is generated by an actuator or by a pump in the treatment fluid circuit.

26. The apparatus according to claim 1, wherein the control procedure includes adjustment of the level of blood in the at least one chamber.

* * * * *